United States Patent [19]

Taylor

[11] 4,130,647

[45] Dec. 19, 1978

[54] METHODS FOR TREATING CONGESTIVE HEART FAILURE AND ISCHEMIC HEART DISEASE

[75] Inventor: Colin R. Taylor, Waterford, Conn.

[73] Assignee: Pfizer Inc., New York, N.Y.

[21] Appl. No.: 814,267

[22] Filed: Jul. 8, 1977

[51] Int. Cl.² ............................................. A61K 31/505
[52] U.S. Cl. ...................................................... 424/251
[58] Field of Search ......................................... 424/251

[56] References Cited

U.S. PATENT DOCUMENTS

| | | | |
|---|---|---|---|
| 3,511,836 | 5/1970 | Hess | 424/251 |
| 3,769,286 | 10/1973 | Hess | 260/251 Q |

OTHER PUBLICATIONS

Cohen et al., J. Clin. Pharmacol, 10, p. 408 (1970).

*Primary Examiner*—Donald B. Moyer
*Attorney, Agent, or Firm*—Connolly and Hutz

[57] ABSTRACT

Methods for the treatment of congestive heart failure and ischemic heart disease using prazosin and trimazosin, and the pharmaceutically acceptable acid addition salts thereof.

6 Claims, No Drawings

METHODS FOR TREATING CONGESTIVE HEART FAILURE AND ISCHEMIC HEART DISEASE

BACKGROUND OF THE INVENTION

1. Field of the Invention

This invention relates to the antihypertensive agents prazosin and trimazosin and their pharmaceutically acceptable acid addition salts and their use in treating congestive heart failure and ischemic heart disease.

2. Description of the Prior Art

Congestive heart failure, regardless of its etiology, is characterized by a distention of the myocardial tissue of the left and/or right ventricles of the heart reducing the efficiency with which the blood is ejected into systemic and/or pulmonary circulations and results in elevated venous pressure, lowered cardiac output and peripheral and pulmonary edema. If left untreated the health of a patient with congestive heart failure could deteriorate to the point where the disease would be fatal.

While there are several medicinals available for the treatment of congestive heart failure, the most widely used is digitalis. As effective as digitalis is in the treatment of this disease, its use is limited because of its slow onset of action and the small difference between the maximum therapeutic and mininum toxic dose levels.

Ischemic heart disease is characterized by the obstruction of the major blood vessels which service the heart, resulting in a decreased oxygen supply to myocardial tissue. During physical stress the reduction in the myocardial oxygen supply results in extreme cardiac pain known as angina pectoris.

Although nitrates, such as nitroglycerin, are the drugs of choice as vasodilators in the treatment of ischemic heart disease, they suffer from a short duration of action.

SUMMARY OF THE INVENTION

A method has now been found for treating congestive heart failure in a human subject having such condition which comprises orally or parenterally administering to said human subject a congestive heart failure treating amount of a compound selected from the group comprising prazosin and trimazosin, and the pharmaceutically acceptable acid addition salts thereof.

In addition, a method has been found for treating ischemic heart disease in a human subject suffering from that disease which comprises orally or parenterally administering to said subject an ischemic heart disease treating amount of a compound selected from the group consisting of prazosin and trimazosin, and the pharmaceutically acceptable acid addition salts thereof.

While congestive heart failure and ischemic heart disease are cardiac complications of hypertension, these conditions quite frequently exist individually or together in a normotensive individual. It is rare, however, that a single antihypertensive drug, such as those of the present invention, can be useful in treating more than one of these cardiac abnormalities. In addition, the antihypertensive compounds of the present invention reduce myocardial oxygen consumption and do not increase heart rate, two extremely important characteristics for medicinal agents used in treating congestive heart failure and ischemic heart disease.

DETAILED DESCRIPTION OF THE INVENTION

As previously mentioned, the antihypertensive compounds of the present method invention are known in the art. Prazosin, 1-(4-amino-6,7-dimethoxy-2-quinazolinyl-4-(2-furanylcarbonyl)piperazine, and its pharmaceutically acceptable acid addition salts are claimed and their preparation described in U.S. Pat. No. 3,511,836, and trimazosin, 2-hydroxy-2-methylpropyl 4-(4-amino-6,7,8-trimethoxy-2-quinazolinyl)-1-piperazinecarboxylate, and its pharmaceutically acceptable acid addition salts in U.S. Pat. No. 3,769,286. The chemical structures of prazosin 1 and trimazosin 2 are as follows:

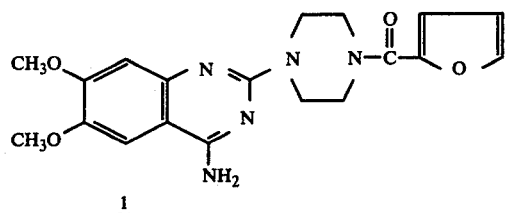

1

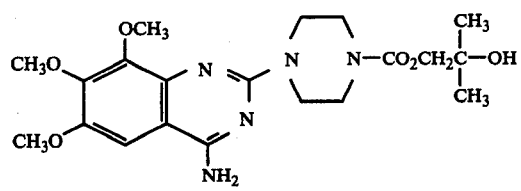

2

Although the generic names of prazosin and trimazosin represent the free base, the present method invention is meant to embrace pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methanesulfate, ethanesulfate, benzenesulfonate and p-toluenesulfonate salts.

In the treatment of congestive heart failure and in treating ischemic heart disease, it is generally preferred to administer prazosin or trimazosin or their pharmaceutically acceptable acid addition salts orally. In using prazosin or one of its pharmaceutically acceptable acid addition salts in congestive heart failure and in the treatment of ischemic heart disease, a dosage level of 3 mg. to 9 mg. per day is therapeutically effective. When using trimazosin or one of its pharmaceutically acceptable acid addition salts in congestive heart failure and in the treatment of ischemic heart disease, a dosage level of 300 mg. to 900 mg. per day is therapeutically effective. A preferred regimen is to administer 1 mg. to 3 mg. of prazosin or one of its pharmaceutically acceptable acid addition salts and 100 mg. to 300 mg. of trimazosin or one of its pharmaceutically acceptable acid addition salts three times a day.

It is to be appreciated that still other variations may also occur in this respect, depending upon the individual response to said medicament, as well as on the particular type of pharmaceutical formulation chosen and the time period and interval at which such administration is carried out. In some instances, dosage levels below the lower limit of the aforesaid range may be more than adequate, while in other cases still larger dosages may be employed without causing any harmful or deleterious side effects to occur provided that such higher dose levels are first divided into several smaller doses that are to be administered throughout the day.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in soft elastic and hard-filled gelatin capsules; preferred materials in this connection also include lactose or milk sugar as well as high molecular weight polyethylene glycols. When aqueous suspension and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin and various like combinations thereof.

Although the preferred mode of administration of the prazosin and trimazosin compounds or one of their pharmaceutically acceptable acid addition salts is oral, they may be administered parenterally as well.

For purposes of parenteral administration, solutions of these particular compounds in sesame or peanut oil or in aqueous-propylene glycol may be employed, as well as sterile aqueous solutions of the corresponding water-soluble acid addition salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter, such as a sintered-glass filter or a diatomaceous-earth or unglazed porcelain filter. Preferred filters of this type include the Berkefeld, the Chamberland and the asbestos disc-metal Seitz filter, wherein the fluid is sucked through the filter candle into a sterile container with the aid of a suction pump. Needless to say, the necessary steps should be taken throughout the preparation of these injectable solutions to ensure that the final products are obtained in a sterile condition.

As considered within the purview of the present invention is the methods of treating congestive heart failure and treating ischemic heart disease in human subjects by orally or parenterally administering to said subjects a therapeutically effective amount of a compound selected from the group of the formulae:

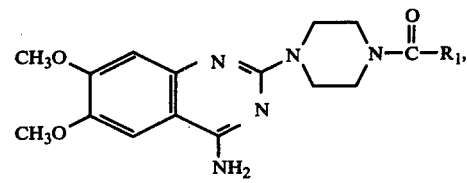

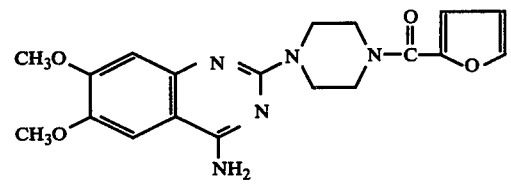

and the pharmaceutically acceptable acid addition salts thereof, wherein $R_1$ is 2-thiazolyl or 2-oxazolyl and Z is a member selected from the group consisting of monoalkylamino and dialkylamino each having up to three carbon atoms in the alkyl moiety, mono($\beta$-hydroxyethyl)amino, and di($\beta$-hydroxyethyl)amino, pyrrolidino, piperidino, homopiperidino and N-substituted piperazino of the formula:

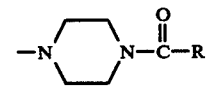

wherein R is chosen from the group consisting of alkoxy having from one to six carbon atoms, alkenyloxy having up to five carbon atoms and hydroxyalkoxy having two to six carbon atoms, alkyl having from one to six carbon atoms, phenyl, naphthyl, furyl and thienyl.

The following examples are provided solely for the purpose of illustration and are not to be construed as limitations of this invention, many variations of which are possible without departing from the spirit or scope thereof. The clinical studies which comprise the following examples were conducted with prazosin or trimazosin wherein the pharmaceutically acceptable hydrogen chloride acid addition salt was employed. For convenience, prazosin hydrochloride and trimazosin hydrochloride are referred to as prazosin and trimazosin, respectively.

EXAMPLE 1

Method

The study comprised ten patients, six males and four females, mean age 51 years (range 46 to 62 years) who had severe ischemic cardiomyopathy and heart failure documented in each by cardiac catheterization and coronary arteriography. The duration of heart failure symptoms ranged from one to six years. All patients were receiving digoxin and diuretics, while seven were also taking long-acting nitrate preparations for the chronic unloading effects of these agents, Williams, et al., *Am. J. Cardiol.*, 39, 84 (1977) and Amsterdam, et al., *Circulation*, 52 [Suppl. 2] 150 (1975).

Each patient had classic electrocardiographic evidence of previous transmural myocardial infarction: four anterior, five combined anterior and inferior, and one inferior-lateral infarction. Left ventriculography confirmed extensive abnormalities of segmental contraction in the appropriate area in each patient and the mean ejection fraction for this group of patients was 0.18 ± 0.03 (SEM). Prior treadmill stress testing was carried out in eight of the ten patients; four did not attain a maximal $VO_2$ of 8.2 ml./kg./min. and four were unable to exceed 13.6 ml./kg./min. and were thereby functional class III (New York Heart Association classification) (Committee on exercise, American Heart Assoc. Exercise Testing and Training: Handbook for Physicians, New York, 1972). The remaining two patients were clinically functional class IV with resting dyspnea and were not able to undergo exercise evaluation.

Hemodynamics: All patients were studied in the postabsorptive state; and informed consent was obtained in each. All cardiac medications including digoxin, diuretics and long-acting nitrates were withheld for at least 24 hours prior to study.

Systemic arterial pressure was measured directly through an intra-arterial Teflon catheter placed into a brachial artery. Right atrial (RA), pulmonary artery (PA) and pulmonary artery wedge (PAW) pressures, and cardiac output (CO) by thermodilution were recorded with the Swan-Ganz catheter. Cardiac outputs were performed in triplicate (less than 10 percent variation) utilizing iced-water and computations were accomplished by a bed-side computer (Santa Barbara, Technology, Inc., Santa Barbara, Calif.).

Derived hemodynamic variables were calculated as follows: stroke work index (SWI) in $gm-m/M^2$ = SI × (AP−LVFP) × 0.0136 here SI = stroke index, AP = mean systemic arterial pressure and LVFP = left ventricular filling pressure either as the mean PAW or PA diastolic pressure, the particular method utilized for this variable remaining constant throughout the study for each patient; total systemic vascular resistance (TSVR) = 80 [(AP−RA)/CO] where 80 converts mm. Hg. to dynes sec. cm.$^{-5}$ and RA = mean RA pressure; pressure.time per minute (PTM) in mm. Hg. sec. per minute = AP × ET × HR where ET = left ventricular ejection time and HR = heart rate.

Plethysmography: Forearm plethysmography was performed in nine of these patients utilizing a mercury-filled rubber strain guage placed around the mid-forearm as previously described in the art [Miller, et al., Circulation, 51, 328 (1975); Miller, et al., Circ. Res., 39, 127 (1976); Mason, et al., Am. Heart J., 64, 796 (1962); Mason, et al., J. Clin. Invest., 43, 532 (1964); and Mason, et al., Circulation, 32, 755 (1965)]. Patients were studied in the supine position with the forearm elevated so that venous pressure in the arm approached zero; the hand vessels were isolated from the forearm by inflation of a wrist cuff to suprasystolic pressures. Forearm venous occlusion was rapidly achieved by inflation of a sphygmomanometer cuff wrapped around the upper arm and attached to a container of compressed air with a special pressure guage preset at 30 mm. Hg. Forearm blood flow was calculated from the change in forearm circumference during acute venous occlusion and was expressed as ml./100 g. of tissue per minute [Mason, et al., Am. Heart J., 64, 796 (1962)]. Simultaneous intra-arterial pressure was obtained from the indwelling brachial artery catheter placed in the opposite arm. Forearm vascular resistance (FVR) was calculated as the ratio of mean arterial pressure to forearm blood flow expressed in units of mm. Hg./ml. per 100 g. per minute. All values for forearm blood flow and FVR were obtained by averaging at least six individual determinations.

Forearm venous tone was determined in the nine patients by the acute occlusion technique [Miller, et al., Circulation, 51, 328 (1975); Miller, et al., Circ. Res., 39, 127 (1976); Mason, et al., Am. Heart J., 64, 796 (1962); Mason, et al., J. Clin. Invest., 43, 532 (1964) and Mason, et al., Circulation, 32, 755 (1965)] utilizing an indwelling 19 guage Teflon catheter or needle placed in a forearm vein immediately distal to the forearm strain guage. The ratio of change in forearm venous pressure to the change in forearm volume expressed in mm. Hg./ml. which occurred during the initial 10 seconds after inflation of the upper arm venous occlusion cuff to 30 mm. Hg. was measured to determine the pressure-volume relations of the capacitance bed. All venous tone determinations were performed in duplicate.

PRAZOSIN ADMINISTRATION

After control hemodynamic and plethysmographic variables were obtained, oral prazosin in a single dose of 2 to 5 mg. was administered in nine patients while one patient demonstrated no alteration in systemic blood pressure or left ventricular filling pressure 2 hours following prazosin and required a second dose of 2 mg. of the drug for a total of 7 mg. All cardiocirculatory variables were remeasured at 30 minute intervals for the succeeding 6 consecutive hours in six patients and 4 hours in three patients. In the one patient requiring two doses of prazosin, measurements commencing 30 minutes after the second dose and continuing 4 hours thereafter were utilized for statistical evaluation. Statistical analysis of these data utilized Student's t test for paired data and analysis of variance.

RESULTS

Hemodynamics: The hemodynamic and peripheral circulatory actions of oral prazosin in all ten patients are summarized in Table I by presentation of variables obtained during the control period and at one, three and six hours following the agent.

Although heart rate tended to decline following prazosin, these changes were not statistically different ($p>0.05$) from the control value of 84 ± 5.1 (SEM) beats per minute. Prazosin lowered mean systemic arterial pressure from 95.3 ± 5.3 to 86.1 ± 5.8 mm. Hg. ($p<0.005$) at 30 minutes and the maximal hypotensive effect was attained at two hours: 76.2 ± 3.8 mm. Hg. (−20%), $p<0.001$ vs. Control (C) (Table I). Thereafter AP remained significantly ($p<0.001$ or $p<0.01$) lowered throughout the observation period although gradually rising toward control.

Left ventricular filling pressure was lowered in all 10 patients 30 minutes post-prazosin and at 60 minutes declined from the control value of 30.2 ± 2.9 to 17.7 ± 1.4 mm. Hg. (−41%) ($p<0.001$ vs. C) (Table I). This variable remained significantly ($p<0.001$) reduced throughout the entire study period.

At 30 minutes following prazosin cardiac index increased in each patient and the mean group value was elevated from 2.07 ± 0.12 to 2.62 ± 0.11 $L/min./M^2$ ($p<0.001$); at 60 minutes the cardiac index attained its maximal increase to 2.94 ± 0.10 $L/min./M^2$ (+42%) ($p<0.001$ vs. C) (Table I). Thereafter this index gradually declined although remaining significantly ($p<0.01$)

elevated at six hours compared to control. Stroke work index was increased (p<0.01) 30 minutes after ingestion of prazosin and reached the peak value of 31.4 ± 5.1 gm.-m/M² (+35%) (p<0.01 vs. C) at 60 minutes. The index of myocardial oxygen demand, pressure.time per minute was reduced from 3293 ± 191 to 2992 ± 208 mm. Hg. sec. per minute (p<0.05) 30 minutes postprazosin and was further lowered to 2793 ± 188 mm. Hg. sec. per minute (−15%) (p<0.001 vs. C) at one hour; thereafter it remained diminished for 6 hours.

Total systemic vascular resistance was reduced in each patient by prazosin (Table I) and the group mean value of 2074 ± 183 dynes sec. cm.⁻⁵ declined to 1448 ± 139 (p<0.001) at 30 minutes, and was maximally lowered to 1156 ± 83 dynes sec. cm.⁻⁵ (−44) (p<0.001 vs. C) one hour post-prazosin. Although there was a gradual rise during the succeeding 5 hours, significant (p<0.001) reduction in TSVR persisted for the entire 6 hour observation (Table I).

Plethysmography: Prazosin produced an increase in forearm blood flow from 1.29 ± 0.14 to 1.71 ± 0.25 ml./100 gm./minute (p<0.05) at 30 minutes and to 1.95 ± 0.33 ml./100 gm./minute (p<0.05 vs. C) at 60 minutes. Forearm blood flow remained increased for the entire 6 hours.

Forearm vascular resistance was lowered by prazosin in all patients at 30 minutes from 88.9 ± 13.8 to 58.4 ± 6.1 mm. Hg./ml./100 gm./min. (p<0.01) and was further reduced to 47.9 ± 5.8 mm. Hg./ml./100 gm./min. (−47%) (p<001 vs. C) one hour post-prazosin. The decline in this variable persisted for the six hour study period.

Venous tone in the forearm was also lowered by prazosin from 58.9 ± 13.8 to 18.5 ± 3.9 ml./mm. Hg. (−69%) (p<0.001 vs. C) by 30 minutes and remained lowered at this level for the entire six hour observation period. The ratio of percent reduction of forearm vascular resistance to percent decline in forearm venous tone [Miller, et al., *Circ. Res.*, 39, 127 (1976)] was 0.49 30 minutes postprazosin and 0.67 at 1 hour, thereby indicating that the drug produced relatively more venodilation than arteriolar dilation. In addition this relationship was essentially unchanged throughout the 6-hour study period indicating that the relative arteriolar and venodilator actions of prazosin remained constant.

TABLE I:

HEMODYNAMIC EFFECTS OF PRAZOSIN IN CONGESTIVE HEART FAILURE

| Patient | Control | | | | | | 1 hour post prazosin | | | | | |
|---|---|---|---|---|---|---|---|---|---|---|---|---|
| | HR | AP | LVFP | CI | SWI | TSVR | HR | AP | LVFP | CI | SWI | TSVR |
| 1 | 66 | 95 | 18 | 2.6 | 41 | 1780 | 66 | 86 | 16 | 2.9 | 41 | 1445 |
| 2 | 72 | 95 | 40 | 1.9 | 20 | 2310 | 72 | 62 | 19 | 2.8 | 23 | 1038 |
| 3 | 86 | 120 | 42 | 1.8 | 22 | 2526 | 90 | 92 | 25 | 3.2 | 34 | 1067 |
| 4 | 98 | 85 | 32 | 1.9 | 14 | 1889 | 105 | 69 | 11 | 3.2 | 24 | 920 |
| 5 | 62 | 108 | 19 | 2.1 | 42 | 2187 | 62 | 91 | 12 | 2.6 | 44 | 1549 |
| 6 | 90 | 107 | 35 | 1.6 | 18 | 2734 | 87 | 77 | 18 | 3.1 | 29 | 1011 |
| 7 | 103 | 87 | 38 | 1.7 | 13 | 2773 | 105 | 67 | 24 | 2.5 | 17 | 1477 |
| 8 | 86 | 75 | 28 | 2.0 | 12 | 1485 | 86 | 64 | 21 | 2.8 | 15 | 908 |
| 9 | 108 | 68 | 32 | 2.9 | 13 | 920 | 102 | 60 | 20 | 2.9 | 20 | 836 |
| 10 | 70 | 112 | 18 | 2.2 | 38 | 2138 | 66 | 110 | 13 | 3.5 | 68 | 1304 |
| Totals (Mean) | 84 | 95.3 | 30.2 | 2.1 | 23.3 | 2074 | 84 | 77.8 | 17.7 | 2.9 | 31.4 | 1156 |
| SEM | ±5 | ±5.3 | ±2.9 | ±.12 | ±3.9 | ±183 | ±5 | ±5.2 | ±1.4 | ±.10 | ±5.1 | ±83 |
| (vs. Control) | | | | | | | ns | <.001 | <.001 | <.001 | <.01 | <.001 |

| Patient | 3 hours post prazosin | | | | | | 6 hours post prazosin | | | | | |
|---|---|---|---|---|---|---|---|---|---|---|---|---|
| | HR | AP | LVFP | CI | SWI | TSVR | HR | AP | LVFP | CI | SWI | TSVB |
| 1 | 66 | 79 | 79 | 3.1 | 45 | 1222 | 70 | 75 | 13 | 3.1 | 38 | 1158 |
| 2 | 70 | 67 | 21 | 2.4 | 25 | 1307 | 72 | 80 | 20 | 2.4 | 27 | 1550 |
| 3 | 85 | 90 | 23 | 2.0 | 32 | 1125 | 90 | 100 | 23 | 2.6 | 30 | 1455 |
| 4 | 100 | 72 | 14 | 2.9 | 22 | 1069 | | | | | | |
| 5 | 61 | 80 | 11 | 2.3 | 36 | 1484 | 56 | 102 | 15 | 2.2 | 45 | 2066 |
| 6 | 72 | 77 | 20 | 2.4 | 26 | 1294 | 78 | 85 | 18 | 2.1 | 25 | 1638 |
| 7 | 112 | 68 | 22 | 2.0 | 16 | 1850 | 86 | 74 | 29 | 2.1 | 15 | 1973 |
| 8 | 80 | 80 | 25 | 2.8 | 17 | 1135 | | | | | | |
| 9 | 99 | 69 | 18 | 3.3 | 24 | 840 | | | | | | |
| 10 | | 104 | 16 | 2.5 | 44 | 1708 | | | | | | |
| Totals (Mean) | 81 | 78.6 | 17.9 | 2.7 | 28.7 | 1303 | 75 | 86.0 | 19.7 | 2.4 | 29.9 | 1639 |
| SEM | ±6 | ±3.6 | ±1.7 | ±.13 | ±3.3 | ±97 | ±5 | ±5.0 | ±2.4 | ±.16 | ±4.3 | ±138 |
| (vs. Control) | ns | <.001 | <.001 | <.001 | <.01 | <.001 | ns | <.01 | <.01 | <.01 | <.01 | <.00 |

DISCUSSION

Clinical application of the physiologic concepts concerning the important role of afterload as a principal determinant of cardiac function has resulted in a valuable new modality for the therapy of severe congestive heart failure [Franciosa, et al., *Lancet*, 1650 (1972)]. However, pharmacologic manipulation of impedance and preload in outpatients with chronic congestive heart failure, though useful, has not been entirely satisfactory. In this regard, the long-acting nitrates generally effect decline in left ventricular filling pressure with relief of congestive symptoms but little or no improvement in cardiac output occurs [Williams, et al., *Am. J. Cardiol.*, 39, 84 (1977)]. In contrast, hydralazine, by reducing impedance may result in an important increase in cardiac output but does not usually lower left ventricular filling pressures [Chatterjee, et al., *Circulation*, 54, 879 (1976)]; hence congestive symptoms are not relieved. In addition, hydralazine has the disadvantage of possessing serologic side effects and leading to sodium retention [Alarcon-Segovia, et al., *Medicine*, 46, 1 (1967)].

The present investigation of the hemodynamic and detailed peripheral circulatory effects of the new antihypertensive agent, prazosin, indicates that this vasodilator exerts nearly immediate as well as prolonged potent dilating actions on both the arterial and venous systems (Table I). The resultant hemodynamic consequences of the primary peripheral circulatory relaxation comprise important salutary effects on both left ventricular filling pressures and cardiac output. Thus prazosin appears to be unique among the currently available oral unloading agents in possessing combined principal effects on both aortic impedance and cardiac preload.

A finding of major importance which emerged from this investigation concerns the relative effects of prazosin on both venous and arteriolar smooth muscle. Prazosin is used clinically as an antihypertensive agent and the arterial dilating actions have been confirmed previously in experimental studies [Cohen, et al., *J. Clin. Pharmacol.*, 10, 408 (1970)]. The important finding delineated herein that prazosin also effects substantial venodilation was of considerable physiologic significance since this unique action on systemic veins allows salutory extension of oral prazosin to the ambulatory therapy of chronic congestive heart failure. In this regard, in patients with normal left ventricular filling pressures, the prazosin-induced venous pooling and decline in cardiac return may lower ventricular preload to such a degree that the point of operation of the ventricle on the Frank-Starling relation is shifted substantially downward and to the left on its ascending limb with resultant decline in cardiac output despite lowered impedance. Furthermore, in the case of prazosin, the attenuation of reflex tachycardia by the agent in this circumstance of lowered stroke volume because of low preload, inhibits the principal regulatory mechanism which would otherwise compensate for the lowered stroke volume. Previous clinical investigations in our laboratories have confirmed that when left ventricular filling pressures are allowed to fall below the upper limits of normal during nitroprusside infusion, cardiac output usually declines [Miller, et al., *Circulation*, 51, 328 (1975)]. A similar phenomenon is observed following sublingual nitroglycerin [Miller, et al., *Circulation*, 51, 421 (1975)]. It would appear that patients who are volume depleted by diuretics would be particularly susceptible to orthostatic hypotension when receiving prazosin and nitrates [Russek, et al., *J.A.M.A.*, 158, 1017 (1955)]. However, prazosin has proved to be relatively well tolerated during long-term administration in hypertensive patients, presumably due to gradual adjustment of intravascular volume. In the present investigation no syncope or other untoward effects occurred following prazosin; all patients, however, were evaluated over the six hour period while at bed rest in the supine position.

A noteworthy feature of prazosin concerns the agent's fundamental mechanism of action. Thus prazosin acts by inhibition of the enzyme phosphodiesterase in vascular smooth muscle resulting in accumulation of cyclic AMP which in turn causes vasodilation (Hess, Postgraduate Medicine Clinical Symposium Proceedings, 1975, p. 9–17). In the myocardium phosphodiesterase inhibition by prazosin leads to increased levels of cyclic GMP. Consequent to these actions cardiac responsiveness to sympathetic stimulation is blunted, thereby attenuating the vasodepressor reflex occurring subsequent to any decline in systemic blood pressure. Therefore, increases in the rate and force of cardiac contraction do not generally occur despite the agent's potent hypotensive actions. Although febrile polyarthritis has been reported in a single patient receiving prazosin for hypertension [Cairns, Br. Med. J., 2, 1424 (1976)], there have been no reports of serologic side effects resembling hydralazine-induced lupus erythematosus [Alarcon-Segovia, et al., Medicine, 46, 1 (1967)].

The present results indicate that, in addition to the hemodynamically beneficial actions of prazosin, the agent substantially lowers indices of myocardial oxygen utilization. Thus pressure time per minute was significantly ($p < 0.001$) reduced; and moreover, the principal determinants of left ventricular wall tension, preload and ejection impedance, decreased while heart rate remained unchanged. In addition, experimental studies have indicated that prazosin has neither direct nor sympathetically mediated indirect effects on the contractile state of the heart [Cohen, J. Clin. Pharmacol., 10, 408 (1970)]. Therefore, prazosin achieves marked improvement in cardiac performance concomitant with substantial reduction of myocardial needs for oxygen. These findings suggest that prazosin may have special usefulness in the management of patients with congestive heart failure related to ischemic heart disease. However, it should be kept in mind that the prazosin-induced decline in PTM was achieved principally through reduction in systemic pressure; because coronary blood flow is directly related to blood pressure, excessive fall in systemic pressure may aggravate an imbalance in the myocardial oxygen supply-demand relation. Thus, while it appears that the presence of heart failure with attendant elevation of left ventricular filling pressures may protect against excessive hypotension reported to occasionally occur with prazosin [Rosendorff, Br. Med. J., 2, 508 (1976)], initial administration of the drug should be carried out with caution.

The present Example of the cardiocirculatory effects of prazosin over a six hour period indicates that marked and sustained enhancement of hemodynamic variables are achieved in most patients by a single oral dose of the agent. Concerning mechanisms of action, the forearm plethysmographic findings demonstrated that the drug exerts profound vasodilator actions on both the systemic arterial resistance and venous capacitance beds with consequent salutary effects on left ventricular impedance and preload. These important dual actions of prazosin suggest that this long-acting oral agent may be utilized in ambulatory patients with severe congestive heart failure obviating the requirement for combinations of unloading drugs.

EXAMPLE 2

METHODS

Studies were performed in male patients with clinical and radiographic evidence of congestive heart failure due to ischemic or primary cardiomyopathy. To be eligible for the study patients had to have supine systolic blood pressure of at least 100 mm. Hg. and a supine resting cardiac index below 2.5 L/min./m$^2$, as measured by the non-invasive carbon dioxide rebreathing method [Franciosa, et al., *J. Lab. Clin. Med.*, 88, 662 (1976) and Franciosa, et al., *Circulation*, 55, 449 (1977)]. Six patients met these criteria and were selected for the study.

After obtaining written informed consent, patients were entered into a 2 day dose finding period during which single daily doses of trimazosin were given and blood pressure and heart rate monitored for 4 hours. On day one 100 mg. was given; if no response or side effects occurred, 200 mg. was given the next day. For purposes of this study a response was defined as a fall in supine blood pressure to a level equal to 0.2 × control systolic pressure +76 mm. Hg. This formula was arbitrarily chosen so that patients with control systolic blood pressure as low as 100 mm. Hg. would be included, and their pressures could be reduced to 96 mm. Hg. Upon completion to the dose finding period, no trimazosin was given for the next 24 hours to allow for washout of previous doses. After this, hemodynamic studies were performed employing the predetermined doses; if 200 mg. of trimazosin was ineffective, 300 mg. was given for hemodynamic studies.

On the day of hemodynamic studies, diuretics and other vasodilators were withheld but maintenance digitalis doses were given in order to obtain a reasonably steady hemodynamic state. Procainamide was given to the one patient who had been taking it chronically. Right heart catheterization was performed using a triple lumen Swan-Ganz catheter which was inserted percutaneously via an antecubital or femoral vein and positioned with its tip in the pulmonary artery and the proximal lumen in the right atrium [Swan, et al,. *N. Engl. J. Med.,* 283, 447 (1970)]. A brachial artery was cannulated with a short teflon catheter inserted over an 18-guage thin walled needle. Catheters were connected to P23Db Statham pressure transducers and pressures recorded on a Hewlett-Packard multichannel physiological recorder. Transducers were positioned at the mid-chest level with the patient supine, and all measurements were made in this position. Heart rate was monitored from the electrocardiogram. Cardiac outputs were measured by the dye-dilution method using indocyanine green injected into the pulmonary artery and sampled from the brachial artery through a Gilford densitometer connected to the recorder. Forearm venous capacitance was measured by occlusion plethysmography employing a Whitney mercury-in-rubber resistance guage [Cohen, et al., *Clin. Sci.,* 30, 267 (1966) and Mason, et al., *Circulation,* 32, 756 (1965)]. For this determination, the forearm was elevated and suspended in a cradle. The venous occluding cuff was inflated to 30 mm. Hg. and forearm girth allowed to equilibrate over 2–3 minutes. The change in forearm girth at this point was taken as a measure of venous capacitance.

Hemodynamic measurements were made before and at hourly intervals for 4 hours after administration of trimazosin. Pulmonary wedge pressure was taken as occluded pulmonary arterial pressure or pulmonary arterial diastolic pressure. These were not interchanged and only one was used in any given patient. Systemic vascular resistance was calculated as the difference between means systemic arterial and right atrial pressures divided by cardiac output. Pulmonary vascular resistance was calculated as mean pulmonary arterial pressure divided by cardiac output. Urinalysis, complete blood count, platelet count, serum transaminases, lactic dehydrogenase, alkaline phosphatase, bilirubin, blood urea nitrogen, uric acid, calcium, phosphorous, and fasting glucose were obtained before beginning the dose finding period and on the final day of hemodynamic measurements.

Statistical analysis was performed using student's T-test for paired data.

RESULTS

The clinical characteristics of the patients are shown in Table I. All were in class III or IV congestive heart failure (New York Heart Association criteria) at the time of study, all had cardiomegaly, all had decreased cardiac index, and all were on prior treatment with digitalis and diuretics. Ischemic heart disease was diagnosed by a history of typical angina pectoris, documented previous myocardial infarction, or electrocardiographic evidence of previous myocardial infarction. Primary cardiomyopathy was diagnosed in the absence of any other demonstrable cause of congestive heart failure. In addition, both patients with primary cardiomyopathy had histories of excessive alcohol use, and one of these had normal coronary arteriograms on earlier cardiac catheterization.

TABLE I:

| | | | Clinical Characteristics of Patients With Congestive Heart Failure Receiving Oral Trimazosin | | | |
|---|---|---|---|---|---|---|
| Patient No. | Age | Diagnosis | Previous Therapy | Clinical Class* | Cardio-Thoracic Ratio | Screening Cardiac Index (L/min./π |
| 1 | 68 | IHD | Digitalis Hydrochlorothiazide Isosorbide Dinitrate | III | 0.55 | 1.84 |
| 2 | 56 | IHD | Digitalis Furosemide Procainamide | IV | 0.51 | 0.96 |
| 3 | 81 | IHD | Digitalis Furosemide | IV | 0.67 | 1.77 |
| 4 | 68 | IHD | Digitalis Furosemide Isosorbide Dinitrate | III | 0.55 | 1.84 |
| 5 | 50 | PMD | Digitalis Furosemide | IV | 0.58 | 2.42 |
| 6 | 50 | PMD | Digitalis Furosemide Spironolactone Isosorbide Dinitrate | III | 0.59 | 1.30 |
| Mean | 62.2 | — | — | — | 0.58 | 1.69 |
| SEM | 5.0 | — | — | — | 0.02 | 0.21 |

Abbreviations:
IHD = ischemic heart disease
PMD = primary cardiomyopathy
*New York Heart association criteria Results of the dose-finding period are shown in Table II. The 100 mg. dose of trimazosin resulted in significant reduction of systolic blood pressure and heart rate with peak effect observed between 2 and 3 hours after drug administration. This dose produced the desired hypotensive response in 2 patients (nos. 5 and 6) who were not given higher doses. The other four patients were given 200 mg. of trimazosin the following day. Their control systolic blood pressures and heart rates were not significantly different from the previous day's values suggesting no carry-over effects of the first dose given 24 hours earlier. The 200 mg. dose lowered systolic pressure to the desired goal in 2 patients (nos. 1 and 2). Patient no. 4 experienced essentially no fall in supine systolic pressure, but standing systolic pressure fell from 103 to 91 mm. Hg. and was accompanied by orthostatic light-headedness. Hemodynamic studies in this patient were performed using the 200 mg. dose. Patient no. 3 experienced neither the desired reduction in systolic pressure nor side effects and was therefore given 300 mg. of trimazosin for the hemodynamic studies.

TABLE II:

Dose Response to Oral Trimazosin in Patients with Congestive Heart Failure

| Patient | Control Systolic Pressure (mm.Hg.) | Control Heart Rate (beats/min.) | Time to Peak Effect (min.) | Change in Systolic Pressure at Peak (mm.Hg.) | Change in Heart Rate at Peak (beats/min.) |
|---|---|---|---|---|---|
| 100 mg. | | | | | |
| 1 | 106 | 88 | 240 | −4 | −4 |
| 2 | 128 | 98 | 120 | −22 | −4 |
| 3 | 129 | 82 | 180 | −8 | −2 |
| 4 | 107 | 98 | 120 | −4 | −15 |
| 5 | 112 | 98 | 180 | −16 | −10 |
| 6 | 100 | 108 | 90 | −9 | −4 |
| Mean | 113.7 | 95.3 | 155.0 | −10.5 | −6.5 |
| SEM | 4.9 | 3.7 | 22.5 | 2.9 | 2.0 |
| P | | | | <0.02 | <0.05 |
| 200 mg. | | | | | |
| 1 | 116 | 82 | 240 | −21 | 15 |
| 2 | 115 | 90 | 90 | −20 | −3 |
| 3 | 130 | 80 | 210 | −8 | 2 |
| 4 | 100 | 90 | 180 | −1 | −1 |
| 5 | — | — | — | — | — |
| 6 | — | — | — | — | — |
| Mean | 115.3 | 85.5 | 180.0 | −12.5 | 3.3 |
| SEM | 6.1 | 2.6 | 32.4 | 4.8 | 4.0 |
| P | | | | ns | ns |

Following trimazosin administration heart rate tended to fall, and the decrease achieved statistical significance. Mean systemic arterial pressure also fell significantly reaching peak decline at 1.5 hours. At peak effect systolic arterial pressure was reduced from 128.3 × 9.7 (SEM) mm. Hg. to 116.8 ± 9.2 mm. Hg. ($p<0.05$) and diastolic pressure had fallen from 74.8 ± 4.2 mm. Hg. to 67.0 ± 2.9 mm. Hg. (ns). Pulmonary wedge pressure was reduced significantly by 1.5 hours, reaching maximal reduction at 2 hours, but was still significantly below control at 4 hours. Cardiac index was increased maximally and significantly at 1 hour, and tended to remain slightly but not significantly elevated through 4 hours.

Individual hemodynamic responses at peak trimazosin effect are shown in Table III. Since the various hemodynamic parameters showed peak effects at 1–3 hours, 2 hours after administration was arbitrarily chosen as the time of peak hemodynamic effects. Mean systemic and pulmonary arterial pressures were significantly reduced as was pulmonary wedge pressure. At 2 hours cardiac index was increased and systemic vascular resistance was reduced, but these changes were not statistically significant, probably reflecting the small number of observations. Pulmonary arterial pressures fell in every patient but cardiac index failed to increase in 2 patients, 1 who had a normal pulmonary wedge pressure to start, and one who had a normal control cardiac index.

TABLE III:

Hemodynamic Effects of Trimazosin in Patients With Congestive Heart Failure

| Patient No. | Dose of Trimazosin (mg.) | | Heart Rate (beats/min.) | Mean Systemic Arterial Pressure (mm.Hg.) | Mean Pulmonary Arterial Pressure (mm.Hg.) | Pulmonary Wedge Pressure (mm.Hg.) | Cardiac Index (L/min./m$^2$) | Systemic Vascular Resistance (units) | Pulmonary Vascular Resistance (units) |
|---|---|---|---|---|---|---|---|---|---|
| 1 | 200 | C | 87 | 106 | 23 | 12 | 2.11 | 23 | 5 |
|  |  | T | 96 | 82 | 15 | 3 | 1.86 | 23 | 4 |
| 2 | 200 | C | 90 | 83 | 46 | 36 | 0.69 | 53 | 35 |
|  |  | T | 84 | 78 | 39 | 28 | 1.14 | 31 | 18 |
| 3 | 300 | C | 69 | 89 | 35 | 27 | 1.79 | 21 | 10 |
|  |  | T | 75 | 88 | 29 | 23 | 2.36 | 16 | 6 |
| 4 | 200 | C | 81 | 81 | 51 | 38 | 1.64 | 23 | 17 |
|  |  | T | 81 | 87 | 49 | 37 | 1.74 | 24 | 15 |
| 5 | 100 | C | 90 | 106 | 37 | 28 | 3.08 | 17 | 6 |
|  |  | T | 78 | 87 | 31 | 18 | 2.96 | 15 | 6 |
| 6 | 100 | C | 111 | 82 | 52 | 43 | 1.22 | 27 | 22 |
|  |  | T | 96 | 73 | 40 | 34 | 2.67 | 12 | 8 |
| Mean | 183.3 | C | 88.0 | 91.2 | 40.7 | 30.7 | 1.76 | 27.3 | 15.8 |
|  |  | T | 85.0 | 82.5 | 33.8 | 23.8 | 2.12 | 20.2 | 9.5 |
| SEM | 30.7 | C | 5.6 | 4.8 | 4.6 | 4.5 | 0.33 | 5.3 | 4.7 |
|  |  | T | 3.7 | 2.5 | 4.8 | 5.0 | 0.27 | 2.9 | 2.3 |
| P |  |  | ns | <0.05 | <0.01 | <0.01 | ns | ns | <0.05 |

Abbreviations:
C = control
T = 2 hours after trimazosin
ns = not significant

Right atrial pressure fell and forearm veins dilated in every patient following trimazosin administration. Right atrial pressure averaged 11.3 ± 2.1 mm. Hg. before trimazosin and fell to 8.7 ± 1.6 mm. Hg. 2 hours after trimazosin administration. At the same time forearm venous capacitance was increased 35% to an average 1.12 ± 0.22 ml./100 gm. from 0.83 ± 0.18 ml./100 gm. Changes in right atrial pressure and forearm venous capacitance were both statistically significant.

Since cardiac output tended to increase without a rise in heart rate after trimazosin administration, stroke volume was increased. The increase in stroke volume associated with a reduced pulmonary wedge pressure is indicative of improved left ventricular performance. Only one patient failed to shift his left ventricular function curve upward and leftward; instead, stroke volume fell in this patient, who had a normal pulmonary wedge pressure to begin with. In this same patient right atrial pressure fell from 5 to 3 mm. Hg. and forearm venous capacitance increased 50% after trimazosin administration.

DISCUSSION

Trimazosin, a quinazoline derivative, is a new vasodilator. Earlier studies with trimazosin have shown that single oral doses of 50 to 150 mg. significantly lower blood pressure in patients with essential hypertension. [DeGuia, et al., *Curr. Therm. Res.*, 15, 339 (1973)]. The effect was apparent within 30 minutes with peak effect occurring between one and four hours. Mild transient dizziness was the only side effect. No significant effects on heart rate or plasma renin activity were noted. Digital vascular reactivity to norepinephrine infusion was decreased, while norepinephrine uptake and secretion were not affected by trimazosin, suggesting a direct relaxing effect on vascular smooth muscle. It has been suggested that the vasodilator action of trimazosin is confined predominantly to resistance vessels [Vlachakis, et al., *Curr. Ther. Res.*, 17, 564 (1975)].

The present study confirms the previously reported time course of onset, peak and duration of activity after single oral doses of trimazosin [DeGuia, et al., *Curr. Ther. Res.*, 15, 339 (1973)]. Pharmacokinetic studies in man are consistent with these observations as peak plasma concentrations were observed 1–2 hours after an oral dose, with a plasma half life of 3–6 hours.

The hemodynamic effects of trimazosin in patients with congestive heart failure were similar to those produced by other vasodilators in such patients [Miller, et al., *Circulation*, 51, 328 (1975) and Mikulic, et al., *Circulation*, 52, 477 (1975)]. Pulmonary wedge and arterial pressures fell significantly, systemic arterial pressure was reduced modestly, heart rate did not increase, and cardiac output tended to increase, resulting in improved left ventricular performance. In addition, right atrial pressure was reduced and forearm venous capacitance increased, suggesting that trimazosin dilates veins as well as arteries.

The observation that trimazosin did not produce tachycardia in these patients with congestive heart failure is typical of such patients in response to vasodilators. Whereas this finding is somewhat surprising for other vasodilators which do increase heart rate in patients without congestive heart failure, it should be pointed out that trimazosin does not increase heart rate in hypertensives without heart failure [Koshy, et al., *Circulation*, 55, 533 (1977)]. The reason for this is unknown as trimazosin does not possess adrenergic blocking activity. This observation might have important clinical implications since other vasodilators may be contraindicated in patients with compensated ischemic heart disease who may develop tachycardia and increased myocardial oxygen requirements [Sonnenblick, et al., *N. Engl. J. Med.*, 285, 688 (1971)] in response to vasodilators.

In comparison to currently available long-active vasodilators which have been evaluated in patients with congestive heart failure, trimazosin resembles the nitrates. In addition to its effects on right atrial pressure and forearm veins, trimazosin appeared to reduce cardiac output in patients with normal control cardiac output or normal control pulmonary wedge pressure. Vasodilators with venodilating actions may decrease cardiac output because of venous pooling. Nitrates are known venodilators which have consistently lowered ventricular filling pressures, but inconsistently increased cardiac output in patients with congestive heart failure [Mason, et al., *Circulation*, 32, 755 (1965) and Sonnenblick, et al., *N. Engl. J. Med.*, 285, 668 (1971)]. Cardiac output is more likely to fall after nitrate administration if pulmonary wedge pressure is not very high and cardiac output not very low to begin with [Bussman, et al., *Am. J. Cardiol.*, 39, 91 (1977) and Franciosa, et al., *Circulation*, 51, 183 (1975)]. An arterial dilator, such as hydralazine, only slightly reduces pulmonary wedge pressure, but consistently and markedly increases cardiac output in patients with left ventricular failure [Franciosa, et al., *Ann. Intern. Med.*, 86, 388 (1977)]. In addition, hydralazine does not reduce right atrial pressure or dilate forearm veins in such patients.

In conclusion, trimazosin is an orally effective vasodilator which improves ventricular function in patients with congestive heart failure. In addition, it reduces pulmonary arterial and right atrial pressures significantly and increases cardiac output.

EXAMPLE 3

METHODS

Sixteen men between 41 and 66 years of age with chronic left sided congestive heart failure were subjects. Twelve patients had coronary heart disease with an old healed myocardial infarction, one patient had alcoholic cardiomyopathy, and three patients had idiopathic cardiomyopathy as the cause of their chronic heart failure. All 16 patients had cardiomegaly on physical examination and on their chest roentgenogram, a left ventricular third heart sound heard by auscultation, and evidence of pulmonary venous congestion on their chest roentgenogram. Their baseline standing blood pressures ranged between 114 and 150 mm. Hg. systolic and 72 and 100 mm. Hg. diastolic.

The patients received digitalis and diuretic therapy for 6 to 48 months. Their dose of digitalis and diuretic was not changed during this study. Except for potassium chloride, no other medications were taken by any of the 16 patients during this study. All patients signed informed consent forms.

After baseline measurements, all 16 patients received one capsule of single-blind placebo three times daily for two weeks. The patients then received in a double-blind, randomized study trimazosin or placebo for six weeks. Eight patients received one placebo capsule three times daily for weeks one and two, two placebo capsules three times daily for weeks three and four, and three placebo capsules three times daily for weeks five and six of the double-blind period. Seven patients received one 50 mg. trimazosin capsule three times daily for weeks one and two, two 50 mg. trimazosin capsules three times daily for weeks three and four, and three 50 mg. trimazosin capsules three times daily for weeks five and six of the double-blind period. One patient (patient number five on trimazosin) received one 50 mg. trimazosin capsule three times daily for 32 days. His trimazosin dose was not increased after two weeks of this dose because his standing systolic blood pressure was 104/70 mm. Hg.

The patients were seen by one of the investigators, questioned for symptoms, and given a physical examination in the baseline period, at the end of two weeks of single-blind placebo, and at the end of weeks one, two, three, four, five, and six on double-blind medication. A standard 12-lead electrocardiogram and PA and lateral chest roentgenograms were taken in the baseline period, at the end of two weeks of single-blind placebo, and at the end of three weeks and six weeks on double-blind medication.

Two practice treadmill tests were performed by all patients prior to the baseline period. The patients performed a multi-stage uninterrupted treadmill exercise test until the onset of marked dyspnea in the baseline period, and approximately two hours after their morning dose of medication after two weeks of single-blind placebo, after three weeks of double-blind medication, and after six weeks of double-blind medication. The patients exercised at a treadmill speed of 1.7 m.p.h. and a treadmill grade of 0% for the first 3 min., a treadmill speed of 1.7 m.p.h. and a treadmill grade of 10% for the next 3 min., at a treadmill speed of 2.5 m.p.h. and a treadmill grade of 12% for the third 3 min. period, and then at a treadmill speed of 3.4 m.p.h. and a treadmill grade of 14%.

The patients were monitored by telemetry with simultaneous leads II and $V_5$ throughout exercise. Simultaneous leads II and $V_5$ blood pressures were recorded with the patients in the sitting and standing positions immediately before exercise, with the patients in the standing position at the end of each completed stage of exercise and at the end of exercise, and with the patients in the sitting and standing positions every 1 min. for at least 5 min. after the end of exercise. Blood pressures were recorded with a mercury sphygmomanometer.

RESULTS

Pill counts revealed that all 16 patients had taken their medication as prescribed. No adverse effects attributed to medication occurred in any of the 16 patients during the study. Fifteen patients completed the study. One patient (patient number five on trimazosin) developed at rest an acute myocardial infarction with ventricular fibrillation on the thirty-second day of trimazosin therapy. He was successfully resuscitated but died at a community hospital of pump failure two days later. When last seen by one of the investigators four days prior to the myocardial infarction, he was clinically improved on trimazosin and has a blood pressure of 106/70 mm. Hg. in the supine position and 104/70 mm. Hg. in the standing position.

TABLE 1:

| | Exercise Duration in the Baseline, Single-Blind Placebo, and Double-Blind Placebo Periods | | | | | | |
|---|---|---|---|---|---|---|---|
| Pt. no. | Baseline exercise time (sec) | Single-blind placebo exercise time (sec) | Average of baseline and placebo exercise times (sec) | Double-blind placebo (3 weeks) exercise time (sec) | Change from average of baseline and placebo exercise times (%) | Double-blind placebo (6 weeks) exercise time (sec) | Change from average of baseline and placebo exercise times (%) |
| 1 | 506 | 480 | 493 | 465 | −6 | 474 | −4 |
| 2 | 450 | 460 | 455 | 520 | +14 | 580 | +27 |
| 3 | 310 | 325 | 317.5 | 355 | +12 | 325 | +2 |
| 4 | 155 | 205 | 180 | 229 | +27 | 242 | +34 |
| 5 | 198 | 216 | 207 | 227 | +10 | 221 | +7 |
| 6 | 205 | 218 | 211.5 | 224 | +6 | 187 | −12 |
| 7 | 194 | 203 | 198.5 | 215 | +8 | 224 | +13 |
| 8 | 188 | 200 | 194 | 209 | +8 | 237 | +22 |
| Mean | 275.8 | 288.4 | 282.1 | 305.5 | +9.9 | 311.3 | +11.1 |
| ±1 SD | 133.4 | 119.4 | 126.1 | 128.4 | 9.2 | 141.6 | 15.9 |

Table 1 indicates the exercise duration until marked dyspnea for each of the patients randomized to placebo in the baseline period, after 2 weeks of single-blind placebo, after 3 weeks of double-blind placebo, and after 6 weeks of double-blind placebo. Table 2 shows the exercise duration until marked dyspnea for each of the patients randomized to trimazosin in the baseline period, after 2 weeks of single-blind placebo, after 3 weeks of trimazosin, and after 6 weeks of trimazosin.

TABLE 2:

| | Exercise Duration in the Baseline, Single-Blind Placebo, and Double-Blind Trimazosin Periods | | | | | | |
|---|---|---|---|---|---|---|---|
| Pt. no. | Baseline exercise time (sec) | Single-blind placebo exercise time (sec) | Average of baseline and placebo exercise times (sec) | Double-blind trimazosin (3 weeks)* exercise time (sec) | Change from average of baseline and placebo exercise times (%) | Double-blind trimazosin (6 weeks) + exercise time (sec) | Change from average of baseline and placebo exercise times (%) |
| 1 | 160 | 240 | 200 | 180 | −10 | 232 | +16 |
| 2 | 206 | 201 | 203.5 | 428 | +110 | 295 | +45 |
| 3 | 340 | 392 | 366 | 398 | +9 | 406 | +11 |
| 4 | 195 | 172 | 183.5 | 280 | +52 | 435 | +136 |
| 5 | 175 | 195 | 185 | 298 | +61 | — | — |
| 6 | 296 | 270 | 283 | 389 | +37 | 627 | +122 |
| 7 | 356 | 393 | 374.5 | 476 | +27 | 527 | +41 |
| 8 | 244 | 253 | 248.5 | 322 | +29 | 363 | +46 |
| Mean | 246.5 | 264.5 | 255.5 | 346.4 | +39.4 | 412.1 | +59.6 |
| +1 SD | 75.7 | 85.3 | 78.5 | 94.8 | 36.3 | 134.5 | 49.6 |

*trimazosin 300 mg. daily except for 150 mg. daily in patient 5
+trimazosin 450 mg. daily The heart rates were measured from the electrocardiographic recordings.

The data listed in Tables 1–4 were analyzed using Student's t test for independent means. Fisher's exact test was used to analyze the data on improvement of symptoms and the data on changes in roentgenographic evidence of pulmonary venous congestion.

The improvement in exercise duration after three weeks of trimazosin over the average exercise duration during the baseline plus single-blind placebo periods was significantly greater than the improvement in exercise duration after 3 weeks of double-blind placebo over the average exercise duration during the baseline plus single-blind placebo periods ($p < 0.025$). The improvement in exercise duration after 6 weeks of trimazosin over the average exercise duration during the baseline plus single-blind placebo periods was significantly greater than the improvement in exercise duration after 6 weeks of double-blind placebo over the average exercise duration during the baseline plus single-blind placebo periods (p<0.025).

Table 3.

Mean resting and exercise blood pressures and heart rates, exercise-induced ST-segment depression, and cardiothoracic Ratios ± 1 standard deviation during the average baseline plus single-blind placebo periods and during double-blind placebo periods.

| Parameter | Average of Baseline and Single-blind Placebo Periods | Double-blind placebo (3 weeks) | Double-blind placebo (6 weeks) |
|---|---|---|---|
| Resting heart rate (beats/min) | 89.6 ± 8.7 | 87.4 ±10.5 | 87.6 ±10.5 |
| Resting systolic blood pressure (mm Hg) | 123.4 ±10.3 | 123.8 ±11.0 | 120.8 ±7.8 |
| Resting diastolic blood pressure (mm Hg) | 83.6 ± 8.2 | 83.5 ± 7.4 | 82.0 ± 5.2 |
| Resting systolic pressue times heart rate/100 | 110.5 ±12.5 | 108.2 ±17.2 | 105.4 ±11.0 |
| Exercise heart rate (beats/min) | 155.1 ±25.8 | 157.4 ±26.0 | 157.1 ±25.5 |
| Exercise systolic blood pressure (mm Hg) | 155.4 ±14.3 | 156.3 ±13.2 | 154.0 ±13.1 |
| Exercise diastolic blood pressure (mm Hg) | 89.1 ± 7.3 | 89.3 ± 6.2 | 90.0 ± 7.3 |
| Exercise systolic pressue times heart rate/100 | 229.6 ±69.6 | 233.7 ±67.8 | 228.9 ±66.0 |
| Maximal ST-segment depression below resting level (mm) | 1.62 ± 0.57 | 1.69 ± 0.59 | 1.78 ± 0.59 |
| Cardiothoracic ratio | 0.561 ± 0.021 | 0.560 ± 0.027 | 0.561 ± 0.027 |

Table 3 indicates at rest and at the end of exercise the mean heart rate, systolic and diastolic blood pressure, and product of systolic blood pressure times heart rate, the mean maximal amount of exercise-induced ST-segment depression below the resting level, and the mean cardiothoracic ratio during an average of the baseline plus single-blind placebo periods, after 3 weeks of double-blind placebo, and after 6 weeks of double-blind placebo. Table 4 shows at rest and at the end of exercise the mean heart rate, systolic and diastolic blood pressure, and product of systolic blood pressure times heart rate, the mean maximal amount of exercise-induced ST-segment depression below the resting level, and the mean cardiothoracic ratio during an average of the baseline plus single-blind placebo periods, after 3 weeks of trimazosin, and after 6 weeks of trimazosin.

Table 4.

Mean resting and exercise blood pressures and heart rates, exercise-induced ST-segment depression, and cardiothoracic ratios ± 1 standard deviation during the average of baseline plus single-blind placebo periods and during Trimazosin periods

| Parameter | Average of baseline and single-blind Placebo periods | Trimazosin (3 weeks) | Trimazosin (6 weeks) |
|---|---|---|---|
| Resting heart rate (beats/min) | 91.5 ± 9.9 | 86.3 ±9.6 | 86.5 ±7.2 |
| Resting systolic blood pressure (mm Hg) | 129.5 ±8.2 | 116.0 ±9.1 | 112.0 ±8.0 |
| Resting diastolic blood pressure (mm Hg) | 80.4 ±3.3 | 74.3 ±4.9 | 72.5 ±5.2 |
| Resting systolic pressure times heart rate/100 | 119.7 ±11.1 | 100.0 ±13.5 | 96.9 ±10.1 |
| Exercise heart rate (beats/min) | 149.5 ±25.5 | 149.3 ±25.3 | 151.0 ±26.0 |
| Exercise systolic blood pressure (mm Hg) | 154.9 ±15.6 | 156.5 ±17.3 | 154.3 ±15.4 |
| Exercise diastolic blood pressure (mm Hg) | 88.2 ±8.3 | 84.8 ±8.4 | 80.5 ±6.1 |
| Exercise systolic pressure times heart rate/100 | 234.0 ±58.6 | 236.4 ±60.7 | 235.4 ±60.4 |
| Maximal ST-segment depression below resting level (mm) | 1.28 ±0.45 | 1.31 ±0.35 | 1.31 ±0.35 |
| Cardiothoracic ratio | 0.564 ±0.026 | 0.559 ±0.032 | 0.556 ±0.034 |

Table 4.-continued

Mean resting and exercise blood pressures and heart rates, exercise-induced ST-segment depression, and cardiothoracic ratios ± 1 standard deviation during the average of baseline plus single-blind placebo periods and during Trimazosin periods Analysis of the data in Tables 3 and 4 comparing for each parameter the change at 3 weeks and at 6 weeks after trimazosin from the average of the baseline plus single-blind placebo periods with the change at 3 weeks and at 6 weeks after double-blind placebo from the average of the baseline plus single-blind placebo periods revealed no significant differences except for the following. A significant decrease in resting systolic blood pressure (p<0.001), in resting diastolic blood pressure (p<0.025), and in resting product of systolic blood pressure times heart rate (p<0.005) occurred after 3 weeks of trimazosin. A significant decrease in resting systolic blood pressure (p<0.005), in resting diastolic blood pressure (p<0.005), in resting product of systolic blood pressure times heart rate (p<0.01), and in diastolic blood pressure at the end of exercise (p<0.005) occurred after 6 weeks of trimazosin.

Six of the eight patients randomized to trimazosin had a good or excellent improvement in symptoms compared to one of the eight patients randomized to placebo (p=0.020). Four of the eight patients randomized to trimazosin had on their chest roentgenograms disappearance of pulmonary venous congestion compared to none of eight patients randomized to placebo (p=0.038).

DISCUSSION

The results of our double-blind, randomized study in patients with chronic left sided congestive heart failure despite digitalis and diuretic therapy show that in comparison to placebo, trimazosin was effective in lowering resting systolic and diastolic blood pressure and product of systolic blood pressure times heart rate and exercise diastolic blood pressure, in improving clinical symptoms, in improving roentgenographic evidence of pulmonary venous congestion, and in improving exercise tolerance until marked dyspnea. Moreover, the patients tolerated trimazosin 450 mg. daily without occurrence of any side effects.

Impedance reduction with improvement in left ventricular performance was probably responsible for the beneficial effects observed with trimazosin therapy in the patients with chronic heart failure. Hemodynamic studies need to be performed to confirm this.

Although trimazosin has properties similar to hydralazine, unlike hydralazine, it does not produce a reflex tachycardia and has not been associated with adverse effects such as systemic lupus erythematosus.

What is claimed is:

1. A method of treating congestive heart failure in a human subject having such condition which comprises orally or parenterally administering to said human subject a congestive heart failure treating amount of a compound selected from the group consisting of prazosin and trimazosin and the pharmaceutically acceptable acid addition salts thereof.

2. The method of claim 1 wherein the compound is prazosin.

3. The method of claim 1 wherein the compound is trimazosin.

4. A method of treating ischemic heart disease in a human subject suffering from that disease which comprises orally or parenterally administering to said human subject an ischemic heart disease treating amount of a compound selected from the group consisting of prazosin and trimazosin and the pharmaceutically acceptable acid addition salts thereof.

5. The method of claim 4 wherein the compound is prazosin.

6. The method of claim 4 wherein the compound is trimazosin.

* * * * *